United States Patent [19]

Diehl

[11] Patent Number: 5,569,676

[45] Date of Patent: Oct. 29, 1996

[54] METHOD FOR THE TREATMENT OF OSTEOARTHRITIS

[76] Inventor: Harry W. Diehl, 4424 Oak Hill Rd., Rockville, Md. 20853

[21] Appl. No.: 449,066

[22] Filed: May 24, 1995

[51] Int. Cl.$^6$ .......................... A61K 31/22; A61K 31/23
[52] U.S. Cl. .......................... 514/549; 514/552; 514/825; 514/703
[58] Field of Search ........................ 514/703, 825, 514/549, 552

[56] References Cited

U.S. PATENT DOCUMENTS 4,049,824 9/1977 Diehl ........................ 424/312
4,113,881 9/1978 Diehl ........................ 424/312

OTHER PUBLICATIONS

H. W. Diehl & E. L. May, "Cetyl Myristoleate Isolated from Swiss Albino Mice: An Apparant Protective Agent against Adjuvant Arthritis in Rats" Journal of Pharmaceutical Sciences, vol. 83, No. 3, Mar. 1994 pp. 296–299.

The merck Manual, Sixteenth Edition, Merck Research Loaboratories, Merck & Co., Rahway, NJ, pp. 1338–1342 1992.

*Primary Examiner*—Theodore J. Criares
*Attorney, Agent, or Firm*—James J. Brown

[57] ABSTRACT

A method is described for alleviating the symptoms of non-rheumatoid arthritis by administering to the afflicted subject a therapeutically effective amount of cetyl myristoleate either orally, topically, or parenterally.

5 Claims, No Drawings

METHOD FOR THE TREATMENT OF OSTEOARTHRITIS

FIELD OF INVENTION

The present invention is directed to a method for treating non-rheumatoid arthritis. More specifically, the present invention is directed to a method for treating the symptoms of various forms of non-rheumatoid arthritis in mammals by administering either orally, topically, or parenterally a therapeutic effective amount of cetyl myristoleate to the subject mammal.

BACKGROUND OF THE INVENTION

Arthritis is a disease which affects approximately 1 in 7 Americans and which actually encompasses more than one hundred different diseases frequently having entirely different symptoms, causes, and known treatments. Literally, the word arthritis means joint inflammation but has come to encompass disorders that affect not only the joints but other connective tissue of the body including supporting structures such as muscles, tendons, and ligaments as well as the protective coverings of internal organs. Although, as already noted, there are over one hundred different forms of arthritis, some of the most commonly occurring forms of arthritis are osteoarthritis, rheumatoid arthritis, ankylosing spondylitis, rheumatic fever, and gout.

In my earlier U.S. Pat. No. 4,049,824 and 4,113,881, I describe a method for immunizing against rheumatoid arthritis as well as a method for relieving its symptoms. Rheumatoid arthritis is a chronic inflammatory disease of unknown cause in which the joints become inflamed, painful, swollen, and later deformed. In addition, there may be general symptoms such as weakness, fatigue, and loss of appetite. The disease tends to be both chronic and irregular and can be severely disabling.

The aforementioned earlier patents of mine, however, do not address or suggest that the described treatments using cetyl myristoleate could be employed effectively to treat the many other diseases which fall under the general heading of arthritis but which have entirely different causes, symptoms, and known treatments.

The most common form of arthritis is osteoarthritis which is a degenerative joint disease which primarily affects cartilage that covers and cushions the ends of the bones causing it to fray, wear, ulcerate, and in extreme cases, to disappear entirely leaving a bone on bone joint. The disease can result in severe disability particularly in the weight bearing joints such as the knees, hips, and spine. Osteoarthritis is distinguishable, for example, from rheumatoid arthritis in that osteoarthritis involves little or no inflammation and is confined to the joints and surrounding tissue where there is a breakdown or disintegration of cartilage and other tissue thereby making it difficult for the joints to operate properly.

The occurrence of osteoarthritis frequently increases with advancing years. When all ages are considered, men are as frequently affected as women. But in people under age 45, more than twice as many men as women have it and between 55 and 65 more women than men have it. In the above 65 group, there is hardly any difference in the incidence of occurrence.

Accordingly, there is a substantial need for an effective, relatively inexpensive, and easy to administer treatment for forms of arthritis which are non-inflammatory and non-rheumatoid such as the most common form of arthritis, osteoarthritis, as well as the many other forms of the disease which occur. It is therefore an object of the present invention to provide a methodology for treating non-rheumatoid arthritis effectively.

DETAILED DESCRIPTION OF THE INVENTION

In accordance with the present invention, non-rheumatoid arthritis, and especially osteoarthritis, is effectively treated by administering to the afflicted subject a therapeutically effective amount of cetyl myristoleate. The administration of cetyl myristoleate in accordance with the present invention can be accomplished either orally, topically, or parenterally. Depending upon the mode of application, various carriers can be employed to facilitate transport of the cetyl myristoleate into the subject's body. For example, the cetyl myristoleate can be administered topically to the afflicted area in a carrier which is absorbed through the skin such as dimethyl sulfoxide. The cetyl myristoleate, which is normally a liquid at about room temperature, can also be injected. Cetyl myristoleate can also be administered orally in accordance with the present invention in capsules which can, for example, contain one ml. of cetyl myristoleate.

It will be understood, however, that the amount of cetyl myristoleate which is therapeutically effective for particular individuals will depend upon a number of factors including the body weight and condition of the subject, the severity of the form of non-rheumatoid arthritis being treated in accordance with the present invention, the mode of administration of the cetyl myristoleate, and most importantly, the individuals response to the medication. Typically, however, cetyl myristoleate is effectively administered in amount of 0.05 to 0.075 grams per each 140 to 200 grams of body weight. Generally also individuals respond within 3 to 6 weeks time to the cetyl myristoleate so that prolonged dosage with the compound has not proven to be necessary.

EXAMPLE I 12 ml of dimethyl sulfoxide solution containing 1 gram of cetyl myristoleate were administered twice daily for 10 days topically to the hands of an approximately 80 year old male diagnosed as suffering pain in his hands and knees due to osteoarthritis. A dramatic decrease in this pain resulted in 3 to 5 weeks and the individual continued to experience relief from this pain for about four years without requiring further application of medication.

EXAMPLE II

A 250 pound, age 75 year old male diagnosed as suffering from osteoarthritis received four 1 cc capsules of cetyl myristoleate orally, twice with about a two month interval between the dosages. The result was at least a 75% alleviation of pain in the afflicted joints. Only minimal pain persisted following medication in the lower back and hips with the knees, elbows and other joints being almost completely pain free.

EXAMPLE III

A female suffering severe back pain from osteoarthritis applied a 10% solution of cetyl myristoleate in dimethyl sulfoxide topically twice a day until a total of 11 cc had been used. Approximately 90% of the back pain relieved within about a week.

EXAMPLE IV

A 48 year old male suffering from severe osteoarthritis received two 1 c.c injections of liquified cetyl myristoleate at about a two year interval. Prior medication had resulted only in limited relief of the pain resulting from the osteoarthritis. Almost total and persistent relief of pain followed each of the cetyl myristoleate injections.

EXAMPLE V

A 72 year old male diagnosed as having osteoarthritis took three capsules, each containing 1 cc of cetyl myristoleate, followed five months latter by four more of the same capsules. His osteoarthritis was alleviated sufficiently that he was able to discontinue other arthritis medication and resume playing the guitar.

EXAMPLE VI

A 65 year old female suffering from osteoarthritis received four capsules containing 1 cc each of cetyl myristoleate orally. She experienced complete recovery from the osteoarthritis within a short time of taking the medication.

What is claimed is:

1. A method for treating osteoarthritis arthritis in mammals which comprises administering a therapeutically effective amount of cetyl myristoleate to a mammal having osteoarthritis arthritis.

2. The method of claim 1 wherein said cetyl myristoleate is administered in an amount of 0.05–0.75 grams thereof per each 140–200 grams weight of said mammal.

3. The method of claim 1 wherein said cetyl myristoleate is administered in an amount of 0.05–0.75 grams thereof per each 140–200 grams weight of said mammal.

4. The method of claim 1 wherein said cetyl myristoleate is administered orally.

5. The method of claim 1 wherein said cetyl myristoleate is administered parenerally.

* * * * *

UNITED STATES PATENT AND TRADEMARK OFFICE
CERTIFICATE OF CORRECTION

PATENT NO. : 5,569,676  Page 1 of 1
APPLICATION NO. : 08/449066
DATED : October 29, 1996
INVENTOR(S) : Harry W. Diehl It is certified that error appears in the above-identified patent and that said Letters Patent is hereby corrected as shown below:

Column 4, claim 1, line 1 of the claim, "arthritis" should be deleted.

Column 4, claim 1, line 4 of the claim, "arthritis" should be deleted.

Column 4, claim 3, line 2 of the claim, "0.75" should be replaced with --0.075--.

Column 4, claim 5, line 2 of the claim, "parenerally" should be replaced with --parenterally--.

Signed and Sealed this

Sixteenth Day of February, 2010

David J. Kappos
*Director of the United States Patent and Trademark Office*

(12) EX PARTE REEXAMINATION CERTIFICATE (9959th)
United States Patent
Diehl

(10) Number: US 5,569,676 C1
(45) Certificate Issued: Nov. 26, 2013

(54) METHOD FOR THE TREATMENT OF OSTEOARTHRITIS

(75) Inventor: Harry W. Diehl, Rockville, MD (US)

(73) Assignee: Imagenetix, Inc., San Diego, CA (US)

Reexamination Request:
No. 90/011,742, Jun. 15, 2011

Reexamination Certificate for:
Patent No.: 5,569,676
Issued: Oct. 29, 1996
Appl. No.: 08/449,066
Filed: May 24, 1995

Certificate of Correction issued Feb. 16, 2010

(51) Int. Cl.
*A61K 31/21* (2006.01)
*A61K 31/231* (2006.01)

(52) U.S. Cl.
USPC ............ 514/549; 514/552; 514/825; 514/703

(58) Field of Classification Search
None
See application file for complete search history.

(56) References Cited

To view the complete listing of prior art documents cited during the proceeding for Reexamination Control Number 90/011,742, please refer to the USPTO's public Patent Application Information Retrieval (PAIR) system under the Display References tab.

*Primary Examiner* — Evelyn Huang

(57) ABSTRACT

A method is described for alleviating the symptoms of non-rheumatoid arthritis by administering to the afflicted subject a therapeutically effective amount of cetyl myristoleate either orally, topically, or parenterally.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1-5 is confirmed.

\* \* \* \* \*